(12) United States Patent
Palmer et al.

(10) Patent No.: US 6,465,697 B1
(45) Date of Patent: Oct. 15, 2002

(54) CATALYST PROMOTOR FOR THE MANUFACTURE OF POLYPHENOLS

(75) Inventors: David Palmer, Katy; Pui Kwan Wong, Houston, both of TX (US)

(73) Assignee: Resolution Performance Products LLC, Houston, TX (US)

( * ) Notice: Subject to any disclaimer, the term of this patent is extended or adjusted under 35 U.S.C. 154(b) by 0 days.

(21) Appl. No.: 09/834,460

(22) Filed: Apr. 13, 2001

(51) Int. Cl.$^7$ ............................................. C07C 39/16

(52) U.S. Cl. ........................................ 568/728; 568/727

(58) Field of Search ................................. 568/727, 728

(56) References Cited

U.S. PATENT DOCUMENTS

| | | | |
|---|---|---|---|
| 2,468,982 A | 5/1949 | Jansen | 260/619 |
| 2,730,552 A | 1/1956 | Williamson | 260/619 |
| 3,394,089 A | 7/1968 | NcNutt | 260/2.2 |
| 3,972,950 A | 8/1976 | Arien | 568/724 |
| 4,443,635 A | 4/1984 | McLaughlin | 568/728 |
| 4,822,923 A | 4/1989 | Li | 568/724 |
| 4,859,803 A | 8/1989 | Shaw | 568/727 |
| 5,001,281 A | 3/1991 | Li | 568/727 |
| 5,777,180 A | 7/1998 | June | 568/728 |
| 6,013,845 A | 1/2000 | Allan | 568/728 |

Primary Examiner—Michael L. Shippen

(57) ABSTRACT

A process for the manufacture of a polyphenol compound such as bisphenol-A by introducing into a reaction zone a phenolic compound reactant, a carbonyl compound reactant, and a catalyst promoter comprising a dithioketal compound, and reacting the ingredients within the reaction zone in the presence of an acid catalyst.

55 Claims, 1 Drawing Sheet

CATALYST PROMOTOR FOR THE MANUFACTURE OF POLYPHENOLS

FIELD OF THE INVENTION

The present invention relates to a process for the manufacture of polyphenols, and more specifically to the addition of a catalyst promoter to a reaction mixture for the manufacture of polyphenols.

BACKGROUND OF THE INVENTION

The compound 2,2-bis(4-hydroxyphenyl)propane, also called para, para-diphenylolpropane or bisphenol-A, is generally prepared by reacting phenol and acetone in the presence of an acidic condensation catalyst along with a catalyst promoter or cocatalyst to increase the reaction rate and selectivity of the condensation catalyst. U.S. Pat. No. 2,468,982 disclosed the use of mercapto substituted aliphatic carboxylic acids as catalyst promoters to increase the condensation reaction rate between phenols and ketones to such an extent that the reaction time could be cut to $\frac{1}{10}^{th}$ the time previously required. Subsequently, it was discovered that the contact time the acid-catalyzed reaction between phenol and ketones is improved by the use of methyl mercaptans as disclosed in U.S. Pat. No. 2,730,552. Not only was the contact time reduced, but the use of gaseous methyl mercaptan in the reaction zone allowed one to run the reaction with only minimal amounts of catalyst promoter without the formation of any substantial amounts of by-product formation or bisphenol-A product disintegration. Further, methyl mercaptan could be used as a catalyst promoter in a continuous process. It is also distinguished in that its high volatility allows it to be easily separated from the reactor reaction mixture effluent containing bisphenol-A product and avoids the presence of sulfur contaminants in the final product. Since then, the use of gaseous free methyl mercaptan has been the catalyst promoter of choice in acid-catalyzed phenol-acetone reactions.

However, methyl mercaptan is difficult to handle because it is gaseous at room temperature and 1 atmosphere. This makes the shipping of methyl mercaptan inefficient because it must first be pressurized to a liquid state to economically transport sufficient amounts required for the manufacture of bisphenol-A at a plant located some distance from the site producing methyl mercaptan. Moreover, since methyl mercaptan is also hazardous, in some cases shipping this material to certain locations is restricted, resulting in limited availability in these areas. As a result, some bisphenol-A plants must now either produce methyl mercaptan on site, or switch to an alternative catalyst promoter which does not have the volatility of methyl mercaptan.

It is our objective to search for a substance which promotes the acid-catalyzed condensation reaction between phenols and carbonyl compounds at substantially the same rate and with substantially the same selectivity towards bisphenol-A as methyl mercaptan, further without the formation of any by-product sulfur species at levels greater than with the use of methyl mercaptan, but which is not as volatile as methyl mercaptan, which is liquid at room temperature and 1 atmosphere thereby rendering it easily and economically transportable, and which is stable during transport. In essence, we searched for a drop-in replacement for methyl mercaptan which did not possess the shipping and handling disadvantages of gaseous methyl mercaptan.

We originally investigated the use of ethyl mercaptan because it was liquid and is a known catalyst promoter in an acid-catalyzed phenol/ketone reaction. However, the activity of ethyl mercaptan is substantially lower than methyl mercaptan, resulting in longer reaction times. To reduce the reaction time to that of a methyl mercaptan catalyst promoter reaction, three to four times the amount of ethyl mercaptan is needed, resulting in having to use a larger recycle stream containing catalyst promoter back to the reaction zone.

Methyl mercaptan can be converted to its sodium salt in an aqueous solution thereby reducing its volatility and making it much easier to handle and transport. The aqueous salt of methyl mercaptan can also be sent to locations where shipping of pressurized methyl mercaptan in liquid form was restricted. We have also developed a process for regenerating methyl mercaptan from the aqueous salt of methyl mercaptan at the plant location. However, the regeneration of methyl mercaptan adds costs onto the process for making bisphenol-A, and introduces a new effluent stream of sodium acid salt (e.g sodium sulfate or sodium chloride) which must be handled. Accordingly, while the use of aqueous salt of methyl mercaptan solves many of the problems around handling and shipping, it has also introduced a new set of issues which raise the cost of making bisphenol-A by adding gaseous methyl mercaptan to the reaction zone or to one or more reactants.

SUMMARY OF THE INVENTION

We have now discovered a catalyst promoter which can be easily shipped and handled due to its relatively low volatility and stability in liquid state during transport. This catalyst promoter has high activity and high selectivity. The amount of sulfur byproduct species produced using this catalyst promoter is low.

There is now provided a condensation process comprising introducing into a reaction zone ingredients comprising a phenolic compound reactant, a carbonyl compound reactant, and a dithioketal catalyst promoter composition, and condensing the phenolic compound and the carbonyl compound in the presence of an acid catalyst.

There is also provided a process for the manufacture of a polyphenol compound comprising introducing into a reaction zone ingredients comprising a phenolic compound reactant, a carbonyl compound reactant, and a catalyst promoter comprising a dithioketal, and reacting the ingredients within the reaction zone in the presence of an acid catalyst.

There is also provided a synthetic method comprising adding together a phenolic compound, a carbonyl compound, and a dithioketal catalyst promoter, hydrolyzing the dithioketal catalyst promoter to its dissociation products, and condensing the phenolic compound and the carbonyl compound in the presence of an acid catalyst and said dissociation products.

DETAILED DESCRIPTION OF THE INVENTION

Figure 1:
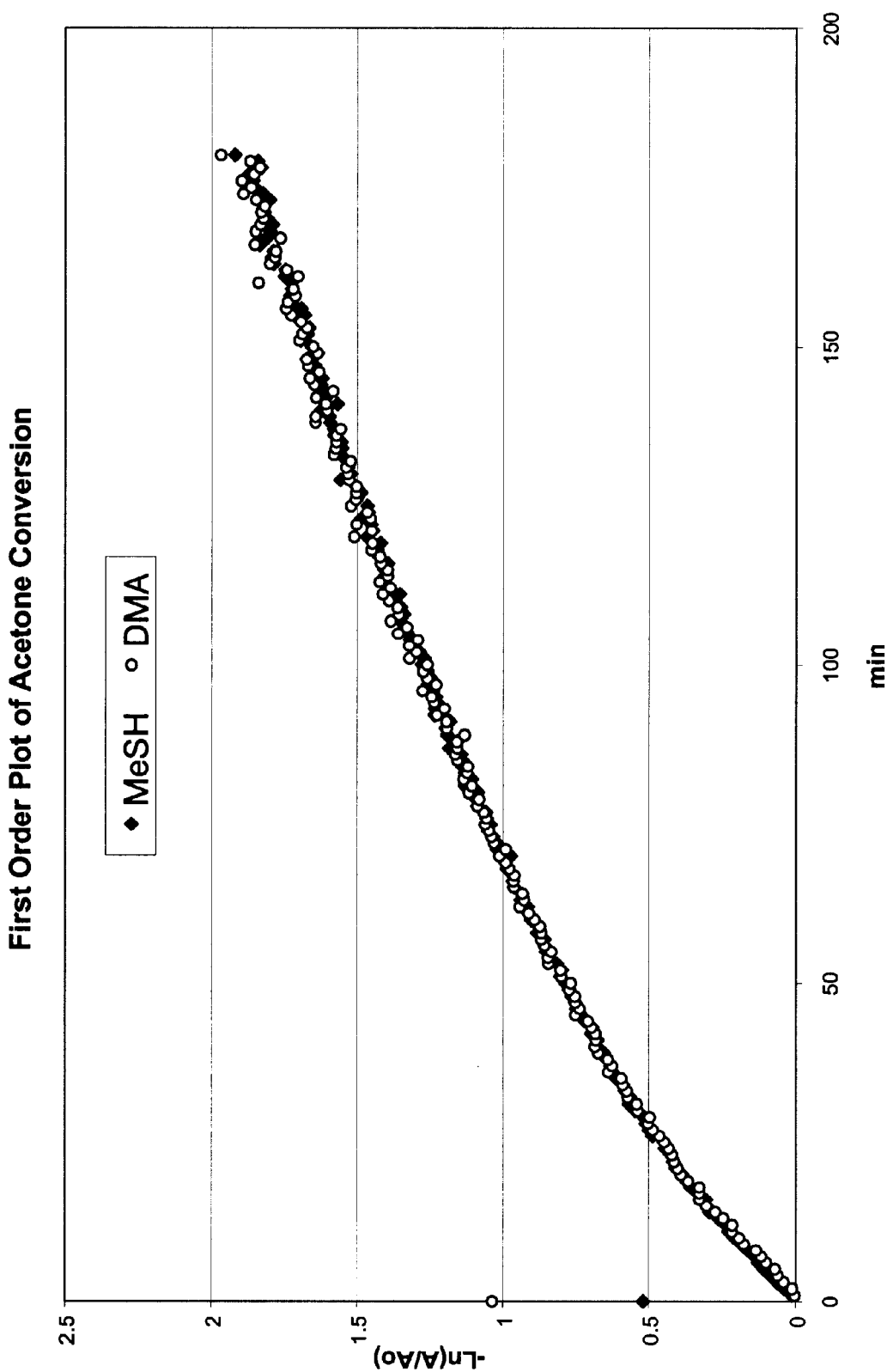
FIG. 1 is a graphical plot of the first order rates for converting acetone in a methyl mercaptan promoted reaction and a 2,2-bis(thiomethyl) propane promoted reaction.

The polyphenols prepared by the process of the invention include those prepared by the reaction of a carbonyl compound reactant. Examples of carbonyl compounds are those compounds represented by the following formula:

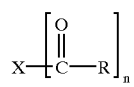

wherein R represents hydrogen or an aliphatic, cycloaliphatic, aromatic, or heterocyclic radical, including hydrocarbon radicals such as alkyl, cycloalkyl, aryl, aralkyl, alkaryl, whether saturated or unsaturated; n is greater than 0, preferably from 1 to 3, more preferably from 1–2, and most preferably is 1; and when n is greater than 1, X represents a bond, or a multivalent linking group having from 1 to 14 carbon atoms, preferably from 1 to 6 carbon atoms, more preferably from 1 to 4 carbon atoms; and when n is 1, X represents hydrogen or an aliphatic, cycloaliphatic, aromatic, or heterocyclic radical, including hydrocarbon radicals such as alkyl, cycloalkyl, aryl, aralkyl, alkaryl, whether saturated or unsaturated, provided that X and R are not both hydrogen.

Suitable carbonyl compounds include aldehydes and ketones. These compounds generally contain from three to fourteen carbon atoms, and are preferably aliphatic ketones. Examples of suitable carbonyl compounds include ketones such as acetone, ethyl methyl ketone, diethyl ketone, dibutyl ketone, isobutyl methyl ketone, acetophenone, methyl and amyl ketone, cyclohexanone, cyclopentanone, 1,3-dichloroacetone and the like. Most preferred is acetone.

The carbonyl compounds are reacted with phenolic compounds. Phenolic compounds are aromatic compounds containing an aromatic nucleus to which is directly bonded at least one hydroxyl group. Suitable phenolic compounds include phenol and the homologues and substitution products of phenol containing at least one replaceable hydrogen atom directly bonded to the aromatic phenol nucleus. Such groups substituting for the hydrogen atom and directly bonded to the aromatic nucleus include the halogen radicals such as chloride and bromide, and the hydrocarbon radicals such as alkyl, cycloalkyl, aryl, alkaryl and aralkyl groups. Suitable phenolic compounds include phenol, the cresols, the xylenols, carvacrol, cumenol, 2-methyl-6-ethyl phenol, 2,4-dimethyl-3-ethylphenol, o-chlorophenol, m-chlorophenol, o-t-butylphenol, 2,5-xylenol, 2,5-di-t-butylphenol, o-phenylphenol, 4-ethylphenol, 2-ethyl-4-methylphenol, 2,3,6-trimethylphenol, 2-methyl-4-tertbutylphenol, 2-tertbutyl-4methylphenol, 2,3,5,6-tetramethylphenols, 2,6-dimethylphenol, 2,6-ditertbutylphenol, 3,5-dimethylphenol, 2-methyl-3,5-diethylphenol, o-phenylphenol, p-phenylphenol, naphthols, phenanthrol, and the like. Most preferred are compositions containing phenol. Mixtures of any of the above may be used.

The above is not meant to limit the invention but to illustrate representative examples of carbonyl compounds and phenolic compounds which are known in the art to make desirable polyphenol and for which those of skill in the art can substitute other similar reactants.

In the preparation of the polyphenols, an excess of the phenolic compound reactant over the carbonyl compound is usually desirable. Generally from about 5 to about 20 moles of phenolic compound per mole of carbonyl compound is desirable for high conversion of the carbonyl compound. Solvents or diluents are not necessary in the preparation of the polyphenol except at low temperature.

The polyphenol compounds obtained by the condensation reaction of a phenolic compound and a carbonyl compound are compounds wherein the nuclei of at least two phenolic radicals are directly attached by carbon to carbon linkages to the same single carbon atom in the alkyl group. An illustrative non-limiting example of a polyphenol compound is represented by the formula:

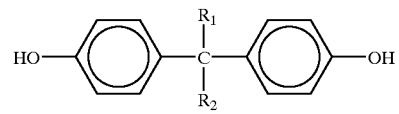

wherein $R_1$ and $R_2$ each independently represent a monovalent organic radical. Examples of such radicals include hydrocarbon radicals such as aliphatic, cycloaliphatic, aromatic, or heterocyclic radical, more specifically hydrocarbon radicals such as alkyl, cycloalkyl, aryl, aralkyl, alkaryl, whether saturated or unsaturated. Preferably, $R_1$ and $R_2$ each independently represent an alkyl radical having from 1 to 2 carbon atoms. Most preferably, the polyphenol compound comprises bis (4-hydroxyphenyl) propane.

Polyphenol compounds are made by the acid-catalyzed reaction between a phenolic compound and a carbonyl compound. The rate and selectivity of the reaction are promoted by introducing into the reaction zone a dithioketal catalyst promoter as such.

In one embodiment, the dithioketal catalyst promoter composition used in the process of the invention is the condensation reaction product between a carbonyl compound and two thiol compounds. In another embodiment, the dithioketal catalyst promoter composition comprises compounds having at least two sulfur atoms covalently bonded to a common carbon atom. In yet another embodiment, the dithioketal catalyst promoter composition comprises dithioketal catalyst promoter compounds represented by the following structure:

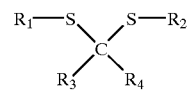

wherein $R_1$, $R_2$, $R_3$, $R_4$ are each independently a branched or unbranched, saturated or unsaturated monovalent organic radical such as an aliphatic, cycloaliphatic, aryl, or heterocyclic radical, including hydrocarbon radicals such as alkyl, cycloalkyl, aryl, aralkyl, and alkaryl; $R_1$ and $R_2$ together may be covalently bonded to form a divalent group, and $R_3$ and $R_4$ together may be covalently bonded to form a divalent group, and one of $R_3$ or $R_4$ may also represent hydrogen. Preferably, $R_1$, $R_2$, $R_3$, $R_4$ are each independently a branched or unbranched, saturated or unsaturated alkyl radical. More preferably, $R_1$, $R_2$, $R_3$, $R_4$ are each independently a saturated alkyl radical each containing from 1 to 4 carbon atoms.

Most preferably, the dithioketal catalyst promoter composition comprises 2,2-bis(thiomethyl)propane compounds represented by the following structure:

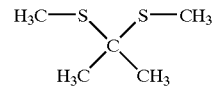

The particular dithioketal catalyst promoter compound chosen is preferably a type which, upon dissociation in the reaction zone, forms the same kind of carbonyl compound as the feed carbonyl compound chosen to make the polyphenol. In one embodiment, the feed carbonyl feed is acetone, and the dithioketal catalyst promoter composition comprises 2,2-bis(thiomethyl) propane, which in the presence of the acid catalyst, dissociates into acetone a methyl mercaptan catalyst promoter.

It is also preferred to choose a particular dithioketal catalyst promoter compound which performs substantially the same as a methyl mercaptan catalyst promoter. In other words, it is desirable to select a dithioketal catalyst promoter which has the same or higher first order rate for converting the carbonyl compound as its dissociation product comprising an alkyl, aryl, alkaryl, or aralkyl mercaptan compound, and more preferably methyl mercaptan. It is also desirable to select a dithioketal catalyst promoter which has the same or higher selectivity toward formation of the polyphenol product as its dissociation product comprising an alkyl, aryl, alkaryl, or aralkyl mercaptan compound, and more preferably methyl mercaptan.

To the reaction vessel is added the phenolic compound, the carbonyl compound, and the dithioketal catalyst promoter composition, and optionally a solvent and water. The acid catalyst, depending upon the type used, may be charged to the reaction vessel or may be loaded into the reaction vessel prior to charging the liquid feeds. The addition sequence of reactants, catalyst promoter, catalyst and optional solvent and water to a reaction vessel is not limited. Further, the manner of introducing the dithioketal catalyst promoter to the reaction mixture is not limited and can take place by the adding the dithioketal catalyst promoter composition to a reaction mixture containing all reactants and catalyst and optional solvent, or to a reaction mixture containing only some of these ingredients, or to any feed stream containing any one of these individual ingredients or a mixture of these ingredients. Thus, the phrase "reaction mixture" when used in conjunction with the introduction of the dithioketal is not limited to the addition of the dithioketal catalyst promoter to a mixture of all the ingredients used to make the polyphenol. Rather, the introduction of the dithioketal catalyst promoter to the reaction mixture includes its addition to any one or a mixture of any one or all of the ingredients used to make the polyphenol.

The process of the invention requires introducing a dithioketal compound which has been isolated as such to the reaction mixture, in contrast to adding a mercaptan, such as methyl mercaptan, to the reaction mixture and in contrast to contacting a phenolic compound and a carbonyl compound with a dithioketal compound formed in situ by, for example, the reaction of acetone with methyl mercaptan.

The reversible formation of 2,2-bis(thiomethyl)propane ("DMA") from methyl mercaptan in and acetone in the presence of an acid catalyst has been reported in *Orq. Chem. of Bilvanet Sulfur: Volume III,* E. Emmet Reid, 1960. The reaction proceeds according to the following equilibrium:

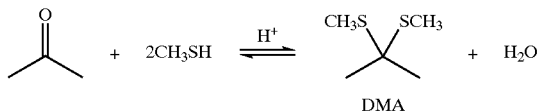

DMA

Instead of adding methyl mercaptan to the reaction mixture, we have added a dithioketal catalyst promoter composition such as 2,2-bis(thiomethyl)propane to the reaction mixture. We have found that the reaction of 2,2-bis(thiomethyl)propane rapidly hydrolyzes and equilibrates to the formation of methyl mercaptan in situ without any induction time. The process of the invention forms methyl mercaptan in situ, thus avoiding the need to isolate, ship and handle methyl mercaptan. Due to the lower volatility and stability of a dithioketal at room temperature and atmospheric conditions, it is more advantageous to isolate, ship and handle the dithioketal and introduce it to the reaction mixture.

To prepare the dithioketal catalyst promoter composition, a carbonyl compound and a thiol compound are reacted together in the presence of an acid catalyst. The carbonyl compound selected may be, and preferably is, the same carbonyl compound used as the feedstock for the preparation of the polyphenol compound. Any acid catalyst as described below may be used. Suitable acid catalysts include Lewis acids such as boron trifluoride etherate, protonic acids such as HCl, and heterogeneous catalysts such as sulfonated styrene-divinylbenzene polymers. For ease of separation, it is preferred to use a heterogeneous catalyst. The stoichiometry is at least two moles of thiol compound to one mole of carbonyl compound. The reaction conditions are not critical, and may proceed at room temperature or at elevated temperatures, or at any pressure, including under autogeneous conditions. The liquid product mixture may be separated from the heterogeneous catalyst, or if a homogeneous catalyst is used, the catalyst is first neutralized.

The dithioketal catalyst promoter composition can be added to the reaction mixture or to any one of the reactants in the liquid phase or in the gaseous phase. Since the dithioketal catalyst promoter composition is in the liquid state during shipping and handling, it is preferred to add it to the reaction mixture or to any reactant in the liquid phase.

The dithioketal catalyst promoter composition should be liquid at room temperature and at 1 atmosphere for ease of shipping and handling. For example, 2,2-bis(thiomethyl) propane is sufficient stable for transportation, it is not readily decomposed at moderate temperatures in the absence of acid catalysts and water, and its thermal decomposition half life at 120° C. was determined to be greater than 40 hours.

The dithioketal catalyst promoter composition is introduced into the reaction mixture neat or in solution. As a solution, the dithioketal may be mixed with a portion or with all the carbonyl compound used to make the polyphenol. The dithioketal catalyst promoter composition may be added directly to the reaction zone, or to any of the streams feeding the reaction zone. It may be added incrementally or continuously over the course of the reaction, or all of the required catalyst promoter may be added to the reaction zone prior to initiating the reaction.

The rate of adding dithioketal catalyst promoter composition to the reactor is not limited. The manner for introducing the dithioketal catalyst promoter composition is also not limited. It may be metered and injected into a feed stream or the reactor vessel, or it may be sprayed into the reactor vessel.

The dithioketal catalyst promoter composition is preferably introduced as a pure composition into the reaction mixture, meaning that outside of those ingredients used to make the polyphenol which are mixed with the dithioketal catalyst promoter, the dithioketal catalyst promoter composition comprises at least 90 wt. % dithioketal, more preferably at least 95 wt. % dithioketal, most preferably at least 98 wt. % dithioketal. Whether or not a pure composition of dithioketal catalyst promoter is used, the amount those impurities present in the dithioketal catalyst promoter composition which are a reactive species with the phenolic compound, the carbonyl compound, or the catalyst, is preferably less than 2 wt. %, more preferably less than 1 wt. %, most preferably less than 0.2 wt. %.

The exact molar amount of the dithioketal catalyst promoter composition as an fresh initial charge to the reaction zone will depend upon the particular reaction conditions employed, the species of dithioketal catalyst promoter selected, and the species of phenolic and carbonyl compounds selected, and the kind of catalyst used. Generally, however, the molar ratio of dithioketal catalyst promoter compound to the carbonyl compound used as the fresh initial charge to the reaction zone in the process of the invention ranges from 0.005:1 up to 0.5:1, preferably from 0.05:1 to 0.25:1. In one embodiment, for the manufacture of bisphenol-A using phenol and acetone as reactants, the molar ratio of dithioketal catalyst promoter compound to the carbonyl compound ranges from 0.025:1 to 0.25:1. The amount of dithioketal catalyst promoter compound added to the reaction mixture is generally about half the molar ratio of a polyphenol-A manufacturing process equipped for the addition of methyl mercaptan since 1 mole of dithioketal catalyst promoter such as 2,2-bis(thiomethyl)propane catalyst promoter yields two moles of the corresponding mono mercaptan catalyst promoter.

Once the reaction zone is charged with the fresh initial charge of the dithioketal composition, for the following reason, the process advantageously requires only small amount of dithioketal as a fresh make-up charge to continue producing the desired yield. The feed stream(s) comprised of the phenolic compound, the carbonyl compound, and the dithioketal catalyst promoter are contacted with an acid catalyst for a period of time sufficient to effect formation of the polyphenol product. In the reaction zone containing the phenolic compound, the carbonyl compound, the acid catalyst, and the dithioketal catalyst promoter, the dithioketal catalyst promoter almost instantly hydrolyzes to its dissociation products, one of which is a mercaptan catalyst promoter. A mercaptan catalyst promoter is any compound having a thiol group covalently bonded to a carbon atom. Once the desired yield of polyphenol is attained by the condensation reaction between the phenolic compound and the carbonyl compound, the resulting crude reaction mixture effluent stream containing the polyphenol product is fed to a separation zone to separate the crude polyphenol compound into a crude polyphenol stream from at least a portion of other compounds such as unreacted carbonyl compounds, unreacted phenolic compounds, the dissociation products of the dithioketal catalyst promoter which include a mercaptan catalyst promoter, and excess water. These compounds may be removed as an overhead or fractionally as draws by way of, for example, distillation or fractional distillation. The method of separation is not limited and can be any conventional method for separating such materials. Distillation is generally the simplest and most preferred method. However, other well known methods can be used independently or in combination with distillation to comprise this separation process.

Any fraction containing dissociation products, one of which is the mercaptan catalyst promoter, may be recycled back to the reaction zone or to any line or reactant feeding the reaction zone. This fraction may be recycled directly back to the reaction zone or may be optionally but preferably further processed to enrich the concentration of and recover the mercaptan catalyst promoter prior to recycling the mercaptan catalyst promoter back to the reaction zone. Depending upon the separation means used, all the overhead may be fed to a mercaptan recovery zone, or a fraction rich in the mercaptan may be fed to a recovery zone, or multiple fractions containing the mercaptan catalyst promoter may be fed to a recovery zone. The means for recovering the mercaptan catalyst promoter are not limited. For example, a stream containing the dissociation products including the mercaptan catalyst promoter compound may be fed to a catalyst promoter. absorber column which comprises a column filled with phenol. In the catalyst promoter absorber column, the catalyst promoter dissociation products are absorbed from the rest of the tops products of the separator. The method of recovering the dissociation product catalyst promoter is not limited and can be any conventional technique, so long as the recovery zone functions to enrich the concentration of the mercaptan catalyst promoter relative to the concentration of the mercaptan catalyst promoter from the separation zone. The separated and recovered catalyst promoter dissociation products containing the mercaptan catalyst promoter compound are generally recycled to the reaction zone by way of a return line.

Substantially all of the mercaptan catalyst promoter can be recycled back to the reaction zone with only minimal losses. Once recycled to the reaction zone, the mercaptan catalyst promoter is just as effective to increase the activity of the acid catalyst and selectively convert the carbonyl compound to the polyphenol product as it was when formed from the dissociation of the dithioketal catalyst promoter compound charged as an fresh initial charge to the reaction zone. Accordingly, after the fresh initial charge of dithioketal to the reaction zone, only a fresh make-up charge of dithioketal catalyst promoter composition is necessary to continue feeding the reaction zone in order to make up for the amount of losses in the course of recovering and recycling the mercaptan catalyst promoter.

Thus, after the fresh initial charge of the dithioketal catalyst promoter composition to the reaction zone, make up charges of the dithioketal catalyst promoter compound may be added to the reaction zone commensurate with the loss rate experienced by the process of separating and recycling the corresponding dissociation products of the dithioketal catalyst promoter back to the reaction zone. Generally, more than 99% of the dissociation product catalyst promoter is recycled, meaning that only 1 wt. % per hour of the dithioketal needs to be charged as a makeup based on the total weight of mercaptan compounds in the reaction system. Higher or lower amounts of the dithioketal catalyst promoter may be introduced as needed.

Accordingly, an additional advantage to using the dithioketal catalyst promoter is that once charged as an fresh initial charge, the catalyst promoter does not have to flow through the process and be discarded or converted or neutralized. The dissociation products of the dithioketal catalyst promoter are easily volatized, completely separated, and can be recycled back to the reaction zone and used as a catalyst promoter.

The polyphenol reaction conditions are any reaction conditions known to those skilled in the art for the manufacture of polyphenols. The specific reaction condition will vary depending on the type of phenolic compound, solvent, carbonyl compound, and condensation catalyst selected. Generally, the phenolic compounds and the carbonyl compounds are reacted in a reaction vessel, whether in the batch or continuous mode, at a temperature ranging from 20° C. to 130° C., preferably from 50° C. to 130° C.

The pressure conditions are not particularly limited and the reaction may proceed at atmospheric, sub atmospheric or super atmospheric pressure. However, it is preferred to run the reaction either without any externally induced pressure, or at sufficient pressure to force the reaction mixture across a catalyst bed or to force the reaction mixture upstream in a vertical reactor, or to maintain the contents of the reaction vessel in a liquid state if the reaction is run at a temperature above the boiling point of any ingredient.

The pressure and temperature should be set under conditions to retain the reactants in the liquid phase in the reaction zone. The temperature may exceed 130° C., but should not be so high as to degrade any of the ingredients in the reaction vessel, nor should it be so high as to degrade the reaction product or promote the synthesis to a substantial amount of unwanted by-products. The contact time ranges from minutes to only 4 hours, or until the desired yield of polyphenol is produced.

The reactants are introduced into the reaction zone under conditions to assure a molar excess of the phenolic compound over the carbonyl compound. Preferably, the phenolic compound is reacted in a substantial molar excess over the carbonyl compound. For example, the molar ratio of the phenolic compound to the carbonyl compound is preferably at least 2:1, more preferably at least 5:1, and up to 25:1. Generally, the molar ratio of phenolic compound to carbonyl compound is maintained at a ratio of 5:1 to 25:1.

Along with the dithioketal catalyst promoter charged into the reaction zone, a small amount of a hydrolyzing agent is required in the reaction zone in order assist the dissociation of the dithioketal catalyst promoter catalyst promoter into its dissociation products, e.g. free mercaptans. A convenient hydrolysis agent is water, which may be introduced into any of the feed charges, directly into the reaction zone, or may be produced in situ by the condensation reaction between the carbonyl compound and the phenolic compound. A molar ratio of water to dithioketal catalyst promoter ranging from 1:1 to 5:1 is sufficient to adequately hydrolyze the dithioketal catalyst promoter. This quantity of water is produced in situ under typical reaction conditions. Thus, additional water does not need to be introduced into the reaction zone, although water may optionally be added if desired.

The reaction is normally conducted in an acidic medium at a pH ranging from 1 to 5. The condensation catalysts used in the process of the invention are any acidic catalysts known for condensing a phenolic compound with a carbonyl compound to make a polyphenol. The acid catalysts may be homogeneous catalysts or heterogeneous catalysts. Acid homogeneous catalysts include the hydrogen halides such as hydrogen chloride, preferably in the anhydrous state, sulfuric acid, hydrochloric acid, phosphoric acid, hydrobromic acid, hydrofluoric acid, nitric acid, acetyl chloride dimethylsulfate, sulfur dioxide, p-toluene sulfonic acid, boron trifluoride, boron trifluoride complexes, a. and any other acids which have a dissociation constant greater than $10^{-3}$.

The condensation of carbonyl compound and phenolic compound can be conducted using a heterogeneous acid catalyst. These catalysts include the organo polysiloxanes containing sulfonic acid groups, solid perfluorinated polymer catalyst having pendant sulfonic groups which may be partially neutralized, acidic clays, or acidic ion exchange resins having a plurality of pendant sulfonic groups.

The acidic ion exchange resins are often mercaptan modified resins of the type conventionally known in the art which include any compound which will react with the acidic groups of the cation exchange resin to introduce a mercapto substituent into the resin. Suitable mercaptan modifying agents to be bound onto the acid sites of the exchange resin include alkyl mercapto amines such as propylaminopropyl mercaptan, bis-2-(mercaptoethyl)-amine, thiazolidine and the like.

The acidic ion exchange resin's effectiveness in the condensation step of the process of the invention is to some extent influenced by its exchange capacities such that the greater the exchange capacity, the more desirable the resin. Preferably, the cation exchange capacity is at least about 0.5 and, preferably, greater than 4.0 meq/g dry weight. Also, those cation exchange resins having bound cationic exchange groups of the stronger exchange potential acids are preferred for use in the condensation step of the process of the present invention. Acidic cation exchange resins suitable (for optional modification with a mercapto modifying agent) for use in the condensation step of the process of the invention include sulfonated styrene-divinyl-benzene copolymers, sulfonated cross-lined styrene polymers, phenol-formaldehyde-sulfonic acid resins, benzene-formaldehyde-sulfonic acid resins, perfluorinated sulfonic acid resins and the like. These include resins under such tradenames as Amberlites (Rohm and Haas Co.), DOWEX.RTM. (Dow Chemical Co.), Permutit QH (Permutit CO.), Chempro (Chemical Process Co.), catalysts from Purolite, Lewatit (Bayer A. G.), NAFIAN (DuPont) and the like. Strong acid sulfonated styrene-divinylbenzene copolymer resins are preferred.

Commercially available aromatic sulfonic acid resins are generally obtained as sodium salts and are converted to the acid form prior to use. Both macroreticular resins and microreticular resins are useful in the condensation process of the present invention. The choice of resin will of course depend on the starting materials, the reaction conditions and the effect of an individual resin under the conditions selected, which determination and selection is within the skill of the art.

The precise amount of acidic cation exchange resin to be used will vary to some degree depending on the specific resin, feed and conditions used for the process. By way of illustration, sufficient catalyst is loaded into the reaction zone to afford a contact time equivalent to a weight hourly space velocity of 0.1 to 10 $hr^{-1}$. The feed stream comprised of the phenolic compound, the carbonyl compound, and the dithioketal catalyst promoter passes through the resin catalyst for a period of time sufficient to effect formation of the polyphenol depending on the feed rate, size of the resin bed, the particular resin and dithioketal catalyst promoter used and the like as can readily be determined by those of skill in the art.

Any suitable reactor may be used as the reaction zone. The reaction can occur in a single reactor, or in a plurality of reactors connected in series or in parallel. The reactor can be a back mixed or plug flow reactor, and the reaction can be conducted in a continuous or batch mode, and the reactor can be oriented to produce an up-flow or down-flow stream.

The invention is not limited to a particular method for recovering the polyphenol compound, and any method known to those of skill in the art is suitable. Generally, however, the crude reaction mixture effluent from the reaction zone is fed to a separator as mentioned above. The polyphenol product, polyphenol isomers, unreacted phenolic compound, and a small amount of various impurities are removed from the separator as a bottoms product. This bottoms product may be fed to a further separator. While crystallization is a common method of polyphenol separation but any method which can be used to separate polyphenol from the mother liquor can be used depending upon the desired degree of purity of the polyphenol product. Once separated, the mother liquor comprising phenol and polyphenol isomers may be returned to the reaction zone as reactant.

Polyphenol separated from mother liquor in separator can then be sent to yet further separations and purifiers such as the polyphenol recovery process. This can be particularly important where very pure product is required as where BPA is produced for use in the subsequent production of polycarbonates. Generally, such further separations can be beneficially conducted using techniques such as recrystallization.

The invention is illustrated by the following example, which is not meant to limit other examples within the spirit and scope of the invention as described herein.

EXAMPLES

This example demonstrates that the rate, selectivity, and distribution of sulfur species for the acidic resin-catalyzed manufacture of Bisphenol-A by the introduction of free 2,2-bis(thiomethyl)propane as a catalyst promoter behaves substantially the same as with the use of methyl mercaptan (MeSH) added as a catalyst promoter.

Preparation of 2,2-bis(thiomethyl)propane

To a three-neck round bottom flask equipped with a mechanical stirrer and a dry ice cold finger condenser was added 100 g of acetone, 5 g of CT-122, a strongly acidic 2% crosslinked sulfonated styrene divinylbenzene cationic gel exchange resin commercially available from Purolite, and 96 g of methyl mercaptan. After stirring at ambient temperature for 3 h and 40° C. for 1 h, the liquid phase was decanted into 200 ml of methylene chloride and the combined washed mixture washed with 100 ml of water three times, dried over anhydrous magnesium sulfate, and concentrated by rotavap. The residue was fractionally distilled to yield 26 g of 2,2-bis(thiomethyl)propane having a boiling point of 64–66° C. at 27 torr. Analysis of the sample by C13 NMR peaked at δ12.35 corresponding to the presence of the CH13S group, and at δ29.63 corresponding to a CH3 group, and at δ54.47, corresponding to the presence of a quarternary carbon atom.

Rate of Reaction for the Preparation of Bisphenol-A

The rates of the acetone/phenol condensation catalyzed by the strongly acidic cationic exchange resin CT122, and promoted with MeSH and 2,2-bis(thiomethyl)propane ("DMA"), respectively, were measured by in-situ IR. A mixture of phenol, water, and CT122 was preheated to 75° C. in an autoclave at autogeneous pressure, followed by injection with a solution of acetone and a promoter. The relative molar composition of the feed in the MeSH-promoted reaction was 100 moles of phenol, 8.1 moles of acetone, 2.8 moles of water, and 1.04 moles of MeSH. The relative molar composition of the feed in the DMA-promoted reaction was the same except that MeSH was replaced with half the molar amount of DMA. The weight ratio of phenol to CT122 was 100 to 3.17 in both reactions. The mixture was reacted over a period of about 3 hours, during which time the reaction rate was measured. The results are graphically depicted in FIG. 1. The kinetic plot shown in the Figure demonstrates that there is no induction period in the DMA-promoted reaction and its first order rate for conversion of acetone is substantially identical to that of a MeSH-promoted reaction.

Selectivity Analysis

The selectivity of the catalyst promoter solutions to the formation of p,p-BPA were measured by HPLC. The following product distribution data show that replacing MeSH with 2,2-bis(thiomethyl)propane (DMA) has no effect on the selectivity of BPA formation. All numbers are in relative units.

| Promoter | % Acetone conversion | p,p-BPA | o,p-BPA | o,o-BPA | CDA* |
|---|---|---|---|---|---|
| MeSH | 90 | 100 | 3.58 | 0.094 | 0.39 |
| DMA | 90 | 100 | 3.52 | 0.091 | 0.4 |

| Promoter | CDB** | BPX*** | Unk. H**** |
|---|---|---|---|
| MeSH | 0.092 | 1.13 | 0.094 |
| DMA | 0.1 | 1.2 | 0.11 |

*Cyclic Dimer A:

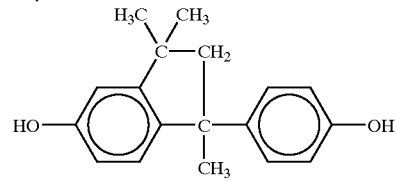

**Cyclic Dimer B:

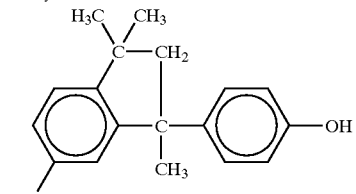

***Trisphenol:

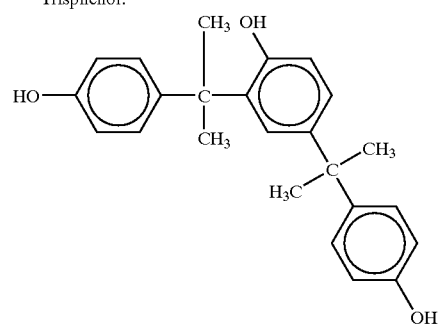

****Hydroxy Cumyl Codimers:

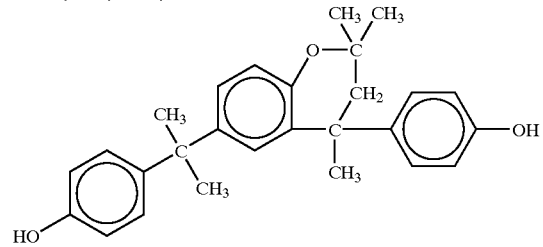

Sulfur Species Analysis

The presence of sulfur by-products in the MeSH and the DMA promoted reaction were measured by GC-MS of the reaction mixtures. Analysis showed the presence of three sulfur species in each case: methyl mercaptan(MeSH), DMA, and 4-thiomethyl-4-methyl-2-pentanone (TMP). The relative concentrations of the three sulfur species are virtually the same in both the MeSH and DMA promoted reactions. This is consistent with rapid equilibration of DMA and MeSH leading to the same distribution of sulfur species under reaction conditions. The small amount of dimethyl disulfide found in the MeSH-promoted reaction was shown to be impurity in MeSH. All numbers are relative areas.

| Promoter | % Acetone conversion | MeSH | DMA | TMP | Dimethyl Disulfide |
|----------|----------------------|------|------|------|--------------------|
| MeSH | 90 | 32.2 | 54.6 | 11.7 | 1.5 |
| DMA | 90 | 37.8 | 51.8 | 10.4 | 0 |

What we claim is:

1. A condensation process comprising introducing into a reaction zone ingredients comprising a phenolic compound reactant, a carbonyl compound reactant, and a dithioketal catalyst promoter composition, and condensing the phenolic compound and the carbonyl compound in the presence of an acid catalyst.

2. The process of claim 1, wherein the phenolic compound comprises phenol, and the carbonyl compound comprises acetone.

3. The process of claim 1, wherein the dithioketal catalyst promoter composition comprises the condensation reaction product between a carbonyl compound and two thiol compounds.

4. The process of claim 1, wherein the dithioketal catalyst promoter composition comprises a compound having at least two sulfur atoms covalently bonded to a common carbon atom.

5. The process of claim 1, wherein the dithioketal catalyst promoter composition comprises a dithioketal catalyst promoter represented by the following structure:

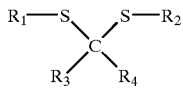

wherein $R_1$, $R_2$, $R_3$, $R_4$ are each independently a branched or unbranched, saturated or unsaturated aliphatic, cycloaliphatic, aryl, or heterocyclic, radical; $R_1$ and $R_2$ together may be covalently bonded to form a divalent group, and $R_3$ and $R_4$ together may be covalently bonded to form a divalent group, and one of $R_3$ or $R_4$ may also represent hydrogen.

6. The process of claim 5, wherein $R_1$, $R_2$, $R_3$, $R_4$ are each independently a branched or unbranched, saturated or unsaturated alkyl radical.

7. The process of claim 6, wherein $R_1$, $R_2$, $R_3$, $R_4$ are each independently a saturated alkyl radical each containing from 1 to 4 carbon atoms.

8. The process of claim 1, wherein the dithioketal catalyst promoter composition comprises 2,2-bis(thiomethyl) propane.

9. The process of claim 1, wherein the dithioketal catalyst promoter composition is a type which dissociates in the reaction zone into the same carbonyl compound as introduced into the reaction zone.

10. The process of claim 1, wherein the carbonyl compound comprises acetone, the phenolic compound comprises phenol, and the dithioketal catalyst promoter composition comprises 2,2-bis(thiomethyl) propane.

11. The process of claim 1, wherein the dithioketal catalyst promoter composition is added in the liquid phase to the reaction mixture or to any reactant.

12. The process of claim 1, wherein the dithioketal catalyst promoter composition is liquid at room temperature and at 1 atmosphere having a thermal decomposition half life at 120° C. greater than 40 hours.

13. The process of claim 1, wherein the dithioketal catalyst promoter composition is introduced into the reaction mixture in solution with a portion or with all the carbonyl compound reactant.

14. The process of claim 1, wherein the dithioketal catalyst promoter composition is introduced as a pure composition into the reaction mixture.

15. The process of claim 14, wherein the dithioketal catalyst promoter composition introduced into the reaction zone comprises at least 95 wt. % dithioketal compound.

16. The process of claim 15, wherein the dithioketal catalyst promoter composition introduced into the reaction zone comprises at least 98 wt. % dithioketal compound.

17. The process of claim 1, wherein the amount of impurities present in the dithioketal catalyst promoter composition which are a reactive species with the phenolic compound reactant, the carbonyl compound reactant, or the acid catalyst, is less than 2 wt. %.

18. The process of claim 1, wherein the amount of impurities present in the dithioketal catalyst promoter composition which are a reactive species with the phenolic compound reactant, the carbonyl compound reactant, or the acid catalyst, is less than 1 wt. %.

19. The process of claim 1, wherein the amount of impurities present in the dithioketal catalyst promoter composition which are a reactive species with the phenolic compound reactant, the carbonyl compound reactant, or the acid catalyst, is less than 0.2 wt. %.

20. The process of claim 1, wherein the molar ratio of dithioketal catalyst promoter to the carbonyl compound used as an fresh initial charge to the reaction zone ranges from 0.025:1 to 0.25:1.

21. The process of claim 1, wherein the dithioketal catalyst promoter hydrolyzes to its dissociation products, one of which is a mercaptan catalyst promoter compound, forming a crude reaction mixture comprising a yield of a polyphenol product produced by condensing the carbonyl compound reactant with the phenolic compound reactant, feeding the crude reaction mixture as an effluent stream from the reaction zone to a separation zone, separating the polyphenol product into a crude polyphenol product stream from at least one fraction comprising the dissociation products of the dithioketal catalyst promoter including said mercaptan catalyst promoter compound, and recycling the mercaptan catalyst promoter back to the reaction zone or to any reactant feeding the reaction zone.

22. The process of claim 21, wherein said fraction is further processed in a recovery zone prior to the recycling step to enrich the concentration of the mercaptan catalyst promoter relative to its concentration in said fraction.

23. The process of claim 21, wherein the molar ratio of dithioketal catalyst promoter to the carbonyl compound used as a fresh initial charge to the reaction zone ranges from 0.025:1 to 0.25:1.

24. The process of claim 22, wherein after said fresh initial charge of the dithioketal catalyst promoter composition to the reaction zone, said reaction zone is fed with a fresh make-up charge of a dithioketal catalyst promoter composition in an amount sufficient to make up for mercaptan catalyst promoter lost during the course of recycling and any optionally recovery of the mercaptan in a recovery zone prior to recycling.

25. The process of claim 24, wherein the amount of make-up dithioketal catalyst promoter compound fed to the reaction zone is 1 wt. % per hour or less based on the total weight of mercaptan compounds.

26. The process of claim 25, wherein the fresh make-up charge comprises a dithioketal catalyst promoter represented by the following structure:

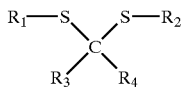

wherein $R_1$, $R_2$, $R_3$, $R_4$ are each independently a branched or unbranched, saturated or unsaturated aliphatic, cycloaliphatic, aryl, or a heterocyclic radical; $R_1$ and $R_2$ together may be covalently bonded to form a divalent group, and $R_3$ and $R_4$ together may be covalently bonded to form a divalent group, and one of $R_3$ or $R_4$ may also represent hydrogen.

27. The process of claim 26, wherein $R_1$, $R_2$, $R_3$, $R_4$ are each independently a branched or unbranched, saturated or unsaturated alkyl radical.

28. The process of claim 27, wherein $R_1$, $R_2$, $R_3$, $R_4$ are each independently a saturated alkyl radical each containing from 1 to 4 carbon atoms.

29. The process of claim 28, wherein the fresh make-up charge comprises 2,2-bis(thiomethyl)propane.

30. The process of claim 1, wherein the acid catalyst comprises an acidic cation exchange resin having a cation exchange capacity of greater than 4.0 meq/g dry weight.

31. The process of claim 1, wherein the contact time of the reactants over the acidic catalyst is equivalent to a weight hourly space velocity of 0.1 to $hr^{-1}$.

32. The process of claim 1, wherein said condensation process yields a polyphenol product comprising bisphenol-A.

33. A process for the manufacture of a polyphenol compound comprising introducing into a reaction zone ingredients comprising a phenolic compound reactant, a carbonyl compound reactant, and a catalyst promoter composition comprising a dithioketal compound, and reacting the ingredients within the reaction zone in the presence of an acid catalyst.

34. The process of claim 33, wherein said polyphenol compound comprises bisphenol-A.

35. The process of claim 33, wherein said dithioketal compound has at least two sulfur atoms covalently bonded to a common carbon atom.

36. The process of claim 33, wherein the dithioketal compound is represented by the following structure:

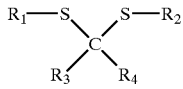

wherein $R_1$, $R_2$, $R_3$, $R_4$ are each independently a branched or unbranched, saturated or unsaturated aliphatic, cycloaliphatic, aryl, or a heterocyclic radical; $R_1$ and $R_2$ together may be covalently bonded to form a divalent group, and $R_3$ and $R_4$ together may be covalently bonded to form a divalent group, and one of $R_3$ or $R_4$ may also represent hydrogen.

37. The process of claim 36, wherein $R_1$, $R_2$, $R_3$, $R_4$ are each independently a branched or unbranched, saturated or unsaturated alkyl radical.

38. The process of claim 37, wherein $R_1$, $R_2$, $R_3$, $R_4$ are each independently a saturated alkyl radical each containing from 1 to 4 carbon atoms.

39. The process of claim 33, wherein the dithioketal compound comprises 2,2-bis(thiomethyl)propane.

40. The process of claim 33, wherein the dithioketal catalyst promoter composition is a type which dissociates in the reaction zone into the same carbonyl compound as introduced into the reaction zone.

41. The process of claim 33, wherein the dithioketal catalyst promoter compound has the same or higher first order rate for converting the carbonyl compound as its dissociation product comprising an alkyl, aryl, alkaryl, or aralkyl mercaptan compound.

42. The process of claim 41, wherein said dissociation product comprises methyl mercaptan.

43. The process of claim 33, wherein the dithioketal catalyst promoter compound has the same or higher selectivity toward formation of bisphenol-A as its dissociation product comprising an alkyl, aryl, alkaryl, or aralkyl mercaptan compound.

44. The process of claim 43, wherein said dissociation product comprises methyl mercaptan.

45. The process of claim 33, wherein the acid catalyst comprises an acidic cation exchange resin having a cation exchange capacity of greater than 4.0 meq/g dry weight.

46. The process of claim 33, wherein the contact time of the reactants over the acidic catalyst is equivalent to a weight hourly space velocity of 0.1 to 10 $hr^{-1}$.

47. The process of claim 33, wherein the polyphenol product consists essentially of bisphenol-A, the carbonyl reactant consists essentially of acetone, the phenolic reactant consists essentially of phenol.

48. The process of claim 47, wherein the dithioketal catalyst promoter compound consists essentially of 2,2-bis(thiomethyl)propane.

49. The process of claim 48, wherein the acid catalyst comprises an acidic cation exchange resin.

50. A synthetic method comprising adding together a phenolic compound, a carbonyl compound, and a dithioketal catalyst promoter, hydrolyzing the dithioketal catalyst promoter to its dissociation products, and condensing the phenolic compound and the carbonyl compound in the presence of an acid catalyst and said dissociation products.

51. The process of claim 50, wherein the product of condensation consists essentially of bisphenol-A, the carbonyl reactant consists essentially of acetone, and the phenolic reactant consists essentially of phenol.

52. The process of claim 51, wherein the dithioketal catalyst promoter compound consists essentially of 2,2-bis(thiomethyl)propane.

53. The process of claim 50, wherein the acid catalyst comprises an acidic cation exchange resin.

54. The process of claim 50, comprising the further addition of water.

55. The process of claim 50, comprising manufacturing water in situ as the agent for hydrolyzing the dithioketal catalyst promoter to its dissociation products.

* * * * *